United States Patent [19]

Loubier et al.

[11] Patent Number: 4,512,354

[45] Date of Patent: Apr. 23, 1985

[54] DENTAL FLOSS APPLICATOR WITH IMPROVED FLOSS SEVERING AND ANCHORING

[76] Inventors: Robert J. Loubier, 5122 Chippewa Ct., Ft. Wayne, Ind. 46804; Robert A. Muhn, 918 Reed Rd., Ft. Wayne, Ind. 46815

[21] Appl. No.: 517,331

[22] Filed: Jul. 26, 1983

Related U.S. Application Data

[63] Continuation-in-part of Ser. No. 435,619, Oct. 20, 1982.

[51] Int. Cl.$^3$ .............................................. A61C 15/00
[52] U.S. Cl. ...................................................... 132/91
[58] Field of Search ............................ 132/91, 92, 93

[56] References Cited

U.S. PATENT DOCUMENTS

| | | | |
|---|---|---|---|
| 2,607,358 | 8/1952 | Maas | 132/92 R |
| 3,903,907 | 9/1975 | Knaus | 132/92 R |
| 4,162,688 | 7/1979 | Tarrson | 132/92 |
| 4,214,598 | 7/1980 | Lee | 132/92 R |

*Primary Examiner*—Gregory E. McNeill
*Attorney, Agent, or Firm*—George A. Gust

[57] ABSTRACT

In a dental floss applicator having a capstan controllable by the user for tensioning the floss and for periodically substituting a fresh floss strand segment for a previously used segment, an improved arrangement for severing floss and anchoring a floss strand end to the capstan as a result of a simple continuous movement of the strand by a user is disclosed. The capstan includes a slot for receiving a one piece metallic clip having a deformation so that the floss strand may be gripped between that deformation and one surface of the capstan slot as well as a cutting prong deformed from the general plane of the clip in the same general direction as the floss gripping deformation and presenting a relatively sharp surface to the floss as the floss is pulled into the gripping position between the deformation and slot. The slot is contoured so that a taut strand of floss is prevented from passing around the wrong surface of the clip or from missing the cutting edge, and the tab which forms the cutting edge cooperates with the slot to hold the clip in position in the slot.

12 Claims, 7 Drawing Figures

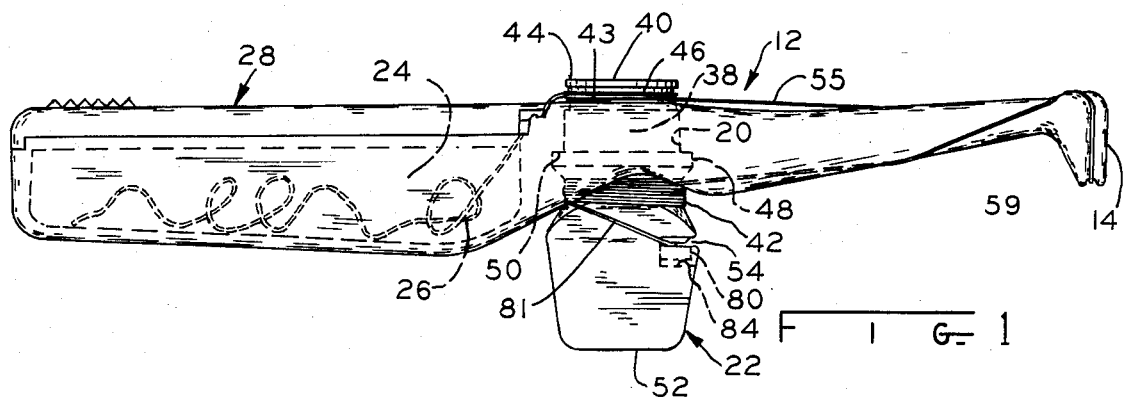
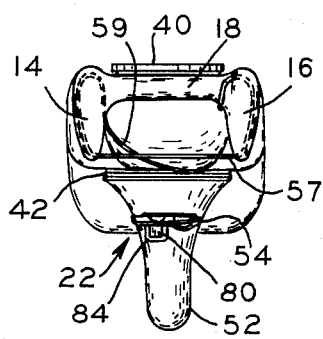
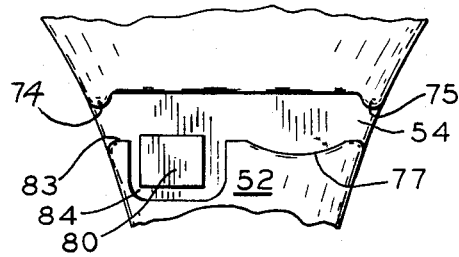
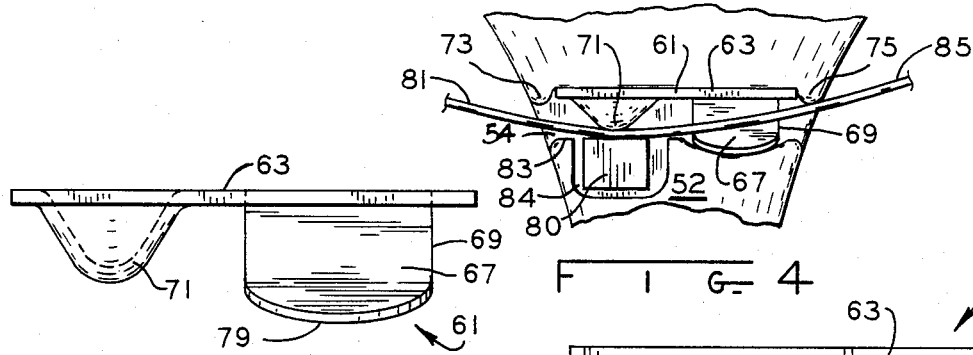
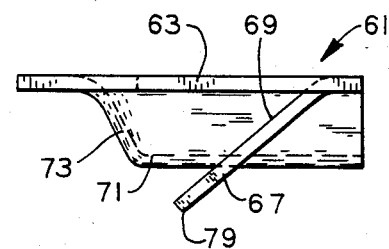
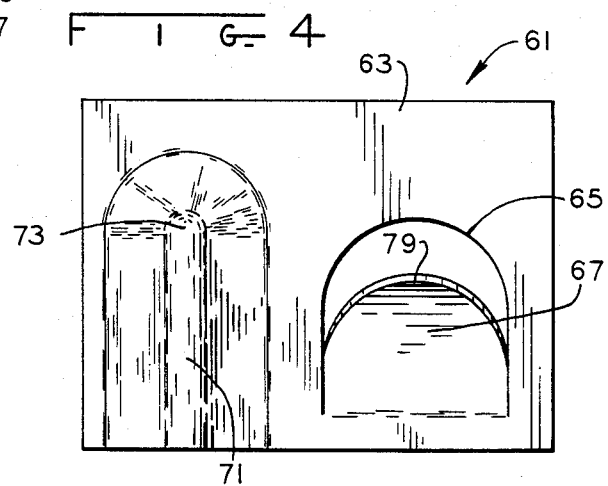

DENTAL FLOSS APPLICATOR WITH IMPROVED FLOSS SEVERING AND ANCHORING

CROSS REFERENCE TO RELATED APPLICATIONS

This application is a continuation-in-part of copending Ser. No. 435,619, filed Oct. 20, 1982, entitled An Improved Dental Floss Applicator, inventor Robert J. Loubier.

BACKGROUND OF THE INVENTION

The present invention relates generally to a strand gripping and severing device and more particularly to such an arrangement in a dental floss applicator to be used in dispensing and supporting a strand of dental floss under tension for cleaning between teeth. Even more particularly, the strand gripping and severing device is formed as a part of a capstan arrangement on the applicator which substitutes fresh floss material for previously used material and maintains the tension on the floss.

U.S. Pat. No. 4,214,598 illustrates dental floss applicators of the general type with which the present invention is primarily concerned while copending U.S. patent application Ser. No. 435,619, filed Oct. 20, 1982, illustrates several improvements on this patented device particularly in the floss strand supply and tensioning aspects thereof. Parent application Ser. No. 435,619 employs a simple capstan V-shaped slot for anchoring the floss leading end while suggesting that the double slotted capstan arrangement with one slot containing a floss severing clip as in the patented arrangement could be employed. These two techniques for anchoring the floss leading end to the capstan in the applicator while adequate, have some drawbacks from a user's point of view. The simplistic single notch arrangement tends to pull free when an inadequate number of turns about the takeup portion of the capstan are employed. Further with the simplistic notch arrangement a separate floss cut off tool is sometimes needed or extra care must be taken to tuck away a free end extending from the notch lest that floss dangle from the free end to the irritation of the user. Similarly, with the two notch arrangement of the prior patent, the half turn of floss between the cut-off notch and the holding notch may slip free of the cutting notch again to the irritation of a user. Ideally, a floss severing function and a floss gripping function would be provided within the same capstan notch.

SUMMARY OF THE INVENTION

Among the several objects of the present invention may be noted the elimination of the above mentioned defects; the achieving of the above noted ideal floss severing and anchoring arrangement; the provision of an arrangement of contemporaneously severing floss and anchoring a floss strand end to a capstan as a result of a simple continuous movement of the strand by a user; the provision of a metallic clip to be inserted into a capstan slot to provide improved anchoring of a floss strand to a capstan; and, an overall improvement in dental floss applicators from a user convenience point of view. These as well as other objects and advantageous features of the present invention will be in part apparent and in part pointed out hereinafter.

In general, a dental floss applicator capstan has a slot which receives a metallic floss severing and anchoring plate. The plate has a gently deformed dimple, which in conjunction with one slot surface defines a floss receiving gap sufficiently narrow to securely grip the floss pulled into the gap. The plate also includes a cutting edge adjacent to and protruding in the same general direction as the dimple so that as a user pulls floss into the slot a floss section is wedged between the dimple and one slot surface while an adjacent floss section engages and is severed by the cutting edge.

BRIEF DESCRIPTION OF THE DRAWINGS

FIG. 1 is a side elevation view of a dental floss applicator embodying the present invention;

FIG. 2 is an end view from the right end of the applicator of FIG. 1;

FIG. 3 is an enlarged view of a portion of FIG. 2 illustration the capstan notch in detail;

FIG. 4 is a view similar to FIG. 3 but showing the metallic floss severing and anchoring plate nested in the slot and the slot receiving a section of floss;

FIG. 5 is a view of the plate of FIG. 4 from the front end as viewed in FIG. 4;

FIG. 6 is a view of the plate of FIG. 5 from the right side thereof; and

FIG. 7 is a view of the plate of FIGS. 5 from the bottom thereof.

Corresponding references characters indicate corresponding parts throughout the several views of the drawing.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENT

Referring to the drawings, the applicator comprises an elongated, rigid body 12 formed of a suitable plastic material such as high density polyethylene. It is shaped as shown, being provided with rounded corners and edges on all parts so as to avoid chafing of the dental floss and to facilitate manipulation. Molded integrally onto one end of the body 12 are furcations 14 and 16 which are generally parallel and spaced apart laterally of the body 12. The adjacent portion of the body 12 is necked down as shown and widens at the end to provide a bridge portion 18 from which the furcations 14 and 16 extend.

About midway between the ends, the body 12 is provided with a cylindrical bearing opening 20 which frictionally receives for rotation a capstan device indicated generally by the numeral 22. The applicator thus far described coincides substantially in design with that of prior application Ser. No. 435,619 except as otherwise shown in the drawings.

To the left side of the capstan device 22 as viewed in FIG. 1 the body 12 is provided with an elongated cavity or chamber 24 which receives a supply of floss-strand 26 either in loose or spool form. A plastic cap 28 is slidably secured to the body 12 over the elongated opening of chamber 24, which is explained in more detail in parent application Ser. No. 435,619.

The capstan device 22 is essentially like that of prior application Ser. No. 435,619. It is a one-piece element preferably molded, made of material hard enough to withstand the compression of floss under tension. Delrin (Dupont trademark for acetal plastic) is an appropriate material. Between the end portions, the capstan device 22 is provided with a journal bearing portion 38 which frictionally fits into the bearing opening 20. On one end is a supply capstan portion 40 and on the other end a takeup capstan portion 42. It will be noted that both portions 40 and 42 project beyond the adjacent sides of the body 12 as shown.

As is also true in the aforesaid application Ser. No. 435,619, the axis of the capstan device 22 may be canted slightly with respect to the longitudinal axis of the body 12. The supply capstan 40 is of a diameter no larger than the journal bearing 38 so that the capstan device 22 may be easily inserted into the bearing opening 20 and removed as may be desired.

The portion 40 is composed of two flanges 43 and 44 and a cylindrical barrel portion 46. The take-up capstan portion 42 also is provided with an annular flange 48 of a size larger than the bearing opening 20 to engage the flat annular surface 50 on the body 12 surrounding the opening 20. The capstan 22 includes a user actuable knob 52 which is near one end of the capstan device 22 and has a notch 54 for securing the strand to the knob as will be described in greater detail subsequently.

Thus, in general, a supply of dental floss 26 resides in the cavity 24 and passes between lid 28 and the body of the applicator in a frictional manner to be tensed then be wound about the upper supply or payout capstan 40 and then in order: strand segment 55 extends from payout capstan 40 to furcation 16, strand segment 57, which is the section used for teeth cleaning purposes, extends from furcation 16 to furcation 14; strand section 59 extends from furcation 14 to the take-up capstan section 42 whereupon the strand is wound about section 42 several times and ultimately the leading end of the floss is neatly tucked away in slot 54.

The slot or notch 54 is of generally uniform cross section as opposed to a tapering or V-shaped configuration as heretofore known. FIG. 1 illustrates notch 54 from a side view while FIGS. 2, 3 and 4 depict that notch from the front or right side of the applicator of FIG. 1. FIGS. 4 and 5 similarly depict a plate 61 from the front or right side of FIG. 1 while FIG. 6 illustrates the plate from the right side of FIG. 5 and FIG. 7 depicts that plate from the bottom of FIGS. 4 and 5.

Turning now to the structural details of the floss severing and anchoring plate 61 as depicted in FIGS. 4, 5, 6 and 7 the plate will be seen to be formed as a generally flat rectangular stainless steel sheet 63 having an arcuate incision 65 which defines a dependent tab portion 67 which is deformed angularly away from the sheet 63 to form the floss cutting edge. While cutting of the floss may occur in various ways depending on how the floss is inserted into notch 54 it is perhaps easiest to think of the somewhat sharp edge 69 of dependent tab 67 as performing the cutting function as floss is drawn into the notch and slides upwardly along the edge 69 toward the apex formed between tab 67 and plate 63. A depression or dimple 71 having gently deformed side portions and leading edge 73 is also depressed downwardly from plate 63 in the same direction as the dependent tab 67. It will be noted particularly in FIGS. 4 and 5 that the dependent tab 67 extends from sheet 63 a distance exceeding the extent of dimple 71 and in fact this distance may be greater than the width of notch 54 for purposes of holding the plate within the notch as will be discussed subsequently.

Returning to FIG. 3, it will be noted that notch 54 includes a pair of downwardly protruding lips 74 and 75 which will serve to both laterally confine and secure the plate 61 within the slot 54 as depicted in FIG. 4 and insure that a floss section pulled tautly into the slot will be properly aligned with the dimple 71 and cutting edge 69 rather than, for example, passing over the top of the plate as viewed in FIG. 4. Slot 54 is also provided with a depression or trough 77 for receiving the tab 67 and further securing plate 61 in position within the slot. Once the plate is properly positioned, an attempt to withdraw the plate will cause the corner 79 to dig into the lower surface of trough 77 to retard removal of the plate 61. The trough 77 also ensures that the lower corner of the tab 67 is well beneath the region in which a taut floss section will be drawn into the slot so as to insure the floss being properly aligned with cutting edge 69 rather than passing beneath tab 67.

Integrally molded in the capstan 22 flush with slot surface 83 is a cantilever block-like spring 80 which is spaced about the two lateral sides and bottom from the body of the capstan 22 by a channel-shaped slot 84. This spring 80 is positioned beneath and in registry with dimple 71 to be engaged thereby as shown. It also is integrally joined at its inner end to such body adjacent the bottom of slot 54.

With the floss wrapped about take up capstan portion 42 and with strand segment 81 passing around knob 52 in the direction of rotation of the capstan which increases floss tension, the floss section 81 passes into notch 54 with a first portion thereof securely gripped between dimple 71 and block spring 80 above slot surface 83 which receive in gripping relation the floss therebetween. The presence of the floss between dimple 71 and spring 80 causes the latter to yield or flex slightly to accommodate the floss thickness, whatever it may be. This is important, because different floss thicknesses are available. Since spring 80 can flex, the floss will be gripped and held regardless of its thickness. Moving in the direction of capstan rotation to increase floss tension, that is from left to right in FIG. 4, it will be seen that the cutting edge 69 angularly precedes the dimple so that continued movement of the floss by the user will ultimately result in strand section 85 being severed by cutting edge 69 with that strand section being discarded by the user and with the applicator ready for service. Angular reversal of the dimple and cutting surfaces would, of course, result in the dimple gripping the floss end which is to be discarded. Thus, the cutting edge must lead the dimple in the direction in which the capstan is to be rotated to increase tension and take up floss.

From the foregoing it is now apparent the a novel improvement in dental floss applicators and in particular in arrangements for contemporaneously severing floss and anchoring a floss strand leading end to a capstan arrangement has been disclosed meeting the objects and advantageous features set out hereinbefore as well as others and that modifications as to the precise configurations, shapes and details may be made by those having ordinary skill in the art without departing from the spirit of the invention or the scope thereof as set out by the claims which follow.

What is claimed is:

1. In a dental floss applicator for use in dispensing and supporting a strand of dental floss under tension for cleaning between teeth of the type having a user actuable capstan for periodically substituting a fresh floss strand segment for a previously used segment and for maintaining strand segment tension during use of the applicator, an arrangement for contemporaneously severing floss and anchoring a floss strand end to the capstan as a result of a simple continuous movement of the strand by a user comprising a slot in the capstan, and a metallic floss severing and anchoring plate nested in the slot, the plate having a gently deformed dimple which in conjunction with one slot surface defines a floss receiving gap sufficiently narrow to securely grip floss pulled into the gap and a cutting edge adjacent to and protruding in the same general direction as the dimple so that as a user pulls floss into the slot, a section of floss is wedged between the dimple and one slot surface while an adjacent floss section engages and is severed by the cutting edge.

2. The arrangement of claim 1 wherein the plate is formed as a generally flat rectangular stainless steel sheet with an arcuate incision defining a dependent tab deformed angularly away from the sheet to form the cutting edge.

3. The arrangement of claim 2 wherein the tab extends from the sheet a distance exceeding the width of the slot in the capstan to thereby cooperate with the slot to secure the plate therein.

4. The arrangement of claim 3 wherein the slot includes a pair of protruding lips on a surface opposite said one surface for laterally confining and securing the sheet in the slot.

5. The arrangement of claim 4 wherein the slot one surface is provided with a tab receiving trough for further securing the plate in position within the slot and for insuring proper alignment of an adjacent floss section with the cutting edge.

6. The arrangement of claim 1 wherein the cutting edge angularly immediately precedes the dimple in the direction of capstan rotation to increase floss tension.

7. The arrangement of claim 1 wherein the slot lies generally along a plane perpendicular to the axis of capstan rotation.

8. The arrangement of claim 1 wherein the slot is provided with deformations for insuring that a taut floss section being drawn into the slot is properly aligned with the dimple and cutting edge.

9. The arrangement of claim 1 wherein the cutting edge protrudes beyond the dimple.

10. In a dental floss applicator for use in dispensing and supporting a strand of dental floss under tension for cleaning between teeth of the type having a user actuable capstan for periodically substituting a fresh floss strand segment for a previously used segment and for maintaining strand segment tension during use of the applicator, an arrangement for anchoring a floss strand end to the capstan as a result of a simple continuous movement of the strand by a user into a slot in the capstan comprising a generally flat rectangular stainless steel sheet having a gently deformed dimple section disposed within the slot and defining in conjunction with an adjacent slot surface a floss receiving gap sufficiently narrow to securely grip floss pulled into the gap, the slot being provided with deformations for securing the stainless steel sheet within the slot and for insuring that a taut floss section being drawn into the slot is properly aligned with the gap.

11. The arrangement of claim 1 wherein said capstan has a cantilever shaped spring element which defines said slot surface and is flexible in a direction away from said dimple whereby said section of floss wedged as aforesaid causes said spring element to flex.

12. The arrangement of claim 11 wherein said capstan is formed of plaster, said spring element on three sides being spaced from the body of said capstan and at the inner end is integral with said body at a location adjacent to the bottom of said slot.

* * * * *